United States Patent
De Ferra et al.

(10) Patent No.: US 7,332,603 B2
(45) Date of Patent: Feb. 19, 2008

(54) PREPARATION OF BIPHOSPHONIC ACIDS AND SALTS THEREOF

(75) Inventors: Lorenzo De Ferra, Rome (IT); Stefano Turchetta, Rome (IT); Pietro Massardo, Rome (IT); Paolo Casellato, Rome (IT)

(73) Assignee: Chemi S.p.A., Cinisello Balsamo (IT)

( * ) Notice: Subject to any disclaimer, the term of this patent is extended or adjusted under 35 U.S.C. 154(b) by 0 days.

(21) Appl. No.: 10/512,930

(22) PCT Filed: Nov. 25, 2002

(86) PCT No.: PCT/IB02/04941

§ 371 (c)(1),
(2), (4) Date: Jul. 13, 2005

(87) PCT Pub. No.: WO03/093282

PCT Pub. Date: Nov. 13, 2003

(65) Prior Publication Data

US 2005/0288509 A1    Dec. 29, 2005

(30) Foreign Application Priority Data

Apr. 29, 2002    (IT)    ............ MI2002A0908

(51) Int. Cl.
C07F 9/22    (2006.01)

(52) U.S. Cl. ............ 546/22; 546/23; 548/112; 562/13

(58) Field of Classification Search ............ 546/22, 546/23; 548/112; 562/13
See application file for complete search history.

(56) References Cited

U.S. PATENT DOCUMENTS

| | | | |
|---|---|---|---|
| 3,262,971 A * | 7/1966 | Matthews ............ | 562/411 |
| 3,366,676 A | 1/1968 | Dyer ............ | 562/22 |
| 4,054,598 A | 10/1977 | Blum et al. ............ | 562/13 |
| 4,267,108 A | 5/1981 | Blum et al. ............ | 548/413 |
| 4,304,734 A | 12/1981 | Jary et al. ............ | 562/13 |
| 4,327,039 A | 4/1982 | Blum et al. ............ | 562/13 |
| 4,407,761 A | 10/1983 | Blum et al. ............ | 562/13 |
| 4,621,077 A | 11/1986 | Rosini et al. ............ | 514/108 |
| 4,922,007 A | 5/1990 | Kieczykowski et al. ............ | 562/13 |
| 5,019,651 A | 5/1991 | Kieczykowski ............ | 562/13 |
| 5,510,517 A | 4/1996 | Dauer et al. ............ | 562/13 |
| 5,792,885 A | 8/1998 | Ham et al. ............ | 562/13 |
| 6,562,974 B2 * | 5/2003 | Cazer et al. ............ | 546/25 |

FOREIGN PATENT DOCUMENTS

| | | |
|---|---|---|
| DE | 37 00 722 | 7/1988 |
| EP | 1205484 | 5/2002 |
| GB | 2 378 444 | 2/2003 |
| SU | 1719405 | 3/1992 |
| WO | WO 98/34940 | 8/1998 |
| WO | WO 00/49026 | 8/2000 |
| WO | WO 01/10874 A1 | 2/2001 |
| WO | WO 01/57052 | 8/2001 |

OTHER PUBLICATIONS

Ezra et al. (2000) "A Peptide Prodrug Approach for Improving Bisphosphonate Oral Absorption" *Journal of Medicinal Chemistry* 43(20):3651-3652.
Mikhalin et al. (1992) Chemical Abstracts, vol. 117, No. 23, Abstract No. 234254.
J. Org. Chem 60 8310 (1995) (will follow) (SP), Kieczykowski et al.
J. Org. Chem 60,8310 (1995) (SP), Kieczykowski et al.

* cited by examiner

*Primary Examiner*—Rosalynd Keys
(74) *Attorney, Agent, or Firm*—Collard & Roe, P.C.

(57) ABSTRACT

A process for preparing alendronate sodium includes the reaction of gammabutyric acid with phosphorous acid and phosphorus trichioride and subsequent treatment with an aqueous solution of an alkali metal hydroxide, in which the reaction is conducted in liquid ionic solvents.

4 Claims, No Drawings

PREPARATION OF BIPHOSPHONIC ACIDS AND SALTS THEREOF

CROSS REFERENCE TO RELATED APPLICATIONS

Applicants claim priority under 35 U.S.C. §119 of Italian Application No. MI2002A000908 filed Apr. 29, 2002. Applicants also claim priority under 35 U.S.C. §365 of PCT/IB02/04941 filed Nov. 25, 2002. The international application under PCT article 21 (2) was published in English.

FIELD OF THE INVENTION

The present invention relates to a process for preparing bisphosphonic acids and their pharmacologically active salts.

STATE OF THE ART

The bisphosphonic acids and their salts, which form the subject of the present patent application are compounds described by the following structural formula:

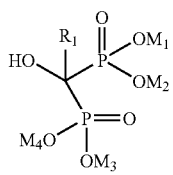

(1)

in which $M_1$, $M_2$, $M_3$, $M_4$ are selected from H, and a monovalent cation. Belonging to this class of molecules are the following compounds used in the treatment of osteoporosis (see Table 1) according to the different meaning that $R_1$ may assume.

TABLE 1

| $R_1 = CH_3$, | Etidronic acid |
| $R_1 = $ imidazol-CH$_2$- | Zoledronic acid |
| $R_1 = $ pyridin-3-yl-CH$_2$- | Risedronic acid |
| $R_1 = $ imidazo[1,2-a]pyridin-3-yl-CH$_2$- | Minodronic acid |
| $R_1 = H_2N-CH_2-CH_2-$ | Pamidronic acid |
| $R_1 = H_2N-(CH_2)_3-CH_2-$ | Alendronic acid |
| $R_1 = H_2N-(CH_2)_4-CH_2-$ | Neridronic acid |

TABLE 1-continued

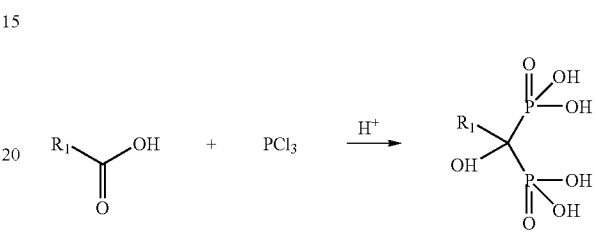

| $R_1 = $ | Olpadronic acid |
| $R_1 = $ | Ibandronic acid |

As regards the methods of synthesis, these compounds are synthesized starting from the corresponding carboxylic acid according to the synthetic scheme appearing in Diagram 1

$$R_1-COOH + PCl_3 \xrightarrow{H^+} R_1-C(OH)(PO(OH)_2)_2$$

Starting from the acid, by subsequent salification of the acid protons, the various salts may be obtained.

A problem that is commonly encountered in the preparation of these compounds is the formation, during the reaction, of very dense unstirrable masses, which render the industrial synthesis of these substances problematical.

In the literature various documents have been published which describe techniques of synthesis of the compounds listed in Table 1.

U.S. Pat. No. 4,621,077, which regards alendronic acid and neridronic acid, describes the use of chlorobenzene as the solvent in the synthesis. The application of this technique leads to obtaining solid and unstirrable masses in the course of the reaction. A series of other patents (U.S. Pat. No. 4,407,761, U.S. Pat. No. 4,327,039, U.S. Pat. No. 4,304,734, U.S. Pat. No. 4,267,108, U.S. Pat. No. 4,054,598) envisages the use of chlorobenzene as reaction solvent, but also in these cases the drawback described above is again met with.

U.S. Pat. No. 4,922,007, U.S. Pat. No. 5,019,651 and U.S. Pat. No. 5,510,517, as well as *J. Org. Chem.* 60, 8310, (1995), envisage the use of methanesulphonic acid as reaction solvent. This makes it possible to obtain stirrable masses in the course of the reaction. However, this technique, as reported in *J. Org. Chem.* 60, 8310, (1995), involves risks of safety in that this solvent gives rise to uncontrollable reactions in the reaction conditions, when the temperature of the reacting mixtures exceeds 85° C. WO9834940 employs polyalkylene glycols as reaction solvents for synthesizing alendronic acid; however, these solvents have a high cost and are difficult to eliminate from the finished product, given their high boiling point In WO0049026, starting from a nitrogen-protected derivative of β-aminopropionic acid to prevent the known problems of stirrability of the reaction mixture, use is made of orthophosphoric acid as the reaction means. The derivatization of the starting product in any case renders the method of synthesis unwieldy and involves the need for introducing additional steps for protection and deprotection.

U.S. Pat. No. 5,792,885 synthesizes pamidronic acid starting from a nitrogen-protected derivative of γ-aminobutyric acid, in aromatic hydrocarbons as the reaction solvents. This method presents the same drawbacks illustrated for the method described in WO0049026.

WO0110874 regards the use of methanesulphonic anhydride as the solvent for producing alendronic acid, but the high cost of the solvent renders the method difficult to apply at an industrial level.

TECHNICAL PROBLEM

The need was thus felt to have available a general process for preparing the compounds described in Table 1 which would not present the drawbacks of the processes known to the art.

SUMMARY OF THE INVENTION

The present applicant has now unexpectedly found that, using as the reaction solvents in the synthesis of the compounds described in Diagram 1 the so-called ionic liquids, it is possible to convert the raw materials into the desired products, avoiding the drawbacks of the processes known to the prior art.

In addition, the solvent used is economically advantageous and easy to recover and recycle.

Consequently, forming the subject of the present invention are processes for preparing the active principles described in Table 1, comprising the reaction of the appropriate raw materials with phosphorous acid and phosphorus trichloride, subsequent treatment with acid water and possible final treatment with an aqueous solution of a hydroxide of an alkaline metal, characterized in that the reaction is conducted in ionic liquids at a temperature of between 15° C. and 120° C.

DETAILED DESCRIPTION OF THE INVENTION $M_1$-$M_4$ are preferably selected from the cations of the alkaline metals, H, cations of aliphatic or cyclolaliphatic amines, and more preferably are sodium and/or H.

The temperature at which the aforesaid ionic solvents are liquid is preferably between 20° C. and 100° C. By liquid ionic solvents are meant the -onium salts selected from the group consisting of ammonium, sulphonium or phosphonium salts.

Possible examples of said solvents are given below:

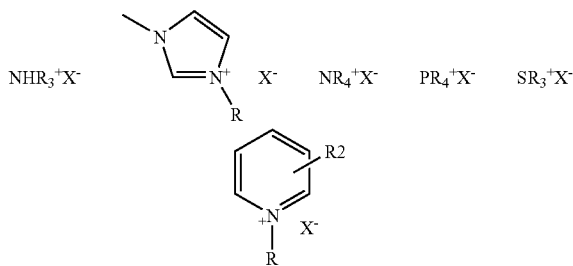

in which each R may be independently H, a linear or branched $C_1$-$C_{20}$ alkyl group, a cycloalkyl containing from 5 to 6 carbon atoms, alkylene aryl, or aryl; $R_2$ is H or a linear or branched $C_1$-$C_{18}$ alkyl group, $X^-$ is an anion selected from the group consisting of halogenide, $BF_4^-$, $PF_6^-$, or $AlCl_4^-$. Particularly preferred is tributylammonium chloride, which melts at approximately 60° C.

These solvents are moreover easy to prepare with methods of a conventional type, do not create problems of safety in so far as they do not cause uncontrollable reactions, and moreover afford the undoubted advantages that they may be recovered and re-used for several production cycles.

The following examples are provided by way of non-limiting illustrations of the process that forms the subject of the present invention.

EXAMPLE 1A

Formation of the Reaction Solvent (Tributylammonium Chloride)

A 3-litre reactor provided with a Dean-Stark trap and drip funnel is charged with 150 ml of toluene and 334.3 g of tributylamine. The solution is cooled to 25-30° C. and from the drip funnel there are added 152.6 ml of 33% aqueous hydrochloric acid, in the meantime controlling that the temperature does not exceed 40° C. The homogeneous solution thus obtained is then distilled in vacuum conditions (50 mmHg) until the internal temperature reaches 80° C. and no more liquid is distilled from the reactor. The mixture thus obtained consists of tributylammonium chloride and is ready for use in the subsequent reactions of formation of bisphosphonic acids.

EXAMPLE 1B

Preparation of Sodium Alendronate

To the liquid phase obtained in Example 1, kept at 70° C., there are added 79.5 g of phosphorous acid and subsequently 100 g of γ-aminobutyric acid. The temperature of the mixture is brought to 60° C., and from the drip funnel there are added 266.4 g of phosphorus trichloride during an interval of approximately one hour, maintaining the internal temperature between 60° C. and 65° C. Subsequently, the reaction mixture is kept under stirring for two hours at 60° C., and then is cooled to 20° C. There are added 410 ml of deionized water, keeping the temperature of the reaction mixture below 40° C. At the end of addition, the temperature is brought up to 90° C. and kept in these conditions for 2 hours. After cooling to 10° C., 1093 ml of 30% aqueous sodium hydroxide are added to the reaction mixture, until the final pH is 11-12. The resulting top layer, consisting of tributylamine is separated off. The tributylamine may be subsequently treated with aqueous hydrochloric acid, as described in Example 1A, to re-obtain tributylammonium hydrochlorate as the reaction solvent.

The aqueous phase is treated with 33% aqueous hydrochloric acid to bring the pH of the solution to 4.3±0.1. The aqueous phase is then dripped on 7000 ml of methanol under stirring, causing the separation of a heavy precipitate, which is then filtered and washed with 500 ml of methanol.

There are obtained 1366 g of crude sodium alendronate, which is then dissolved at 75° C. in 3600 ml of deionized water. The solution is then filtered at 75° C. and left to crystallize by means of slow cooling, until the mixture reaches 5° C. The crystalline solid obtained is filtered and washed with 2×100 ml of deionized water and then dried at 50° C. for 12 hours, to obtain 97.8 g of sodium alendronate (31% yield).

EXAMPLE 2

Preparation of Zoledronic Acid 20 of tributylammonium chloride, prepared as in Example 1A, are put into a 100-ml flask provided with coolant, magnetic stirrer, drip funnel and thermometer. The solid is melted at 60° C., then 3.2 g of phosphorous acid and 5.0 g of 2-(1-imidazyl)-acetic acid are added. The temperature of the mixture is then brought up to 65-70° C., and from the drip funnel there are slowly added 10.9 g of $PCl_3$. Once the addition is completed, the mixture is brought up to 80° C. and kept under these conditions for two hours, at the end of which 20 ml of deionized water are added. The mixture is brought to 90° C. and is kept under these conditions for 2 hours. It is then cooled down to room temperature, and 50 ml of 33% NaOH are added to the mixture, until a pH of the mixture $\geq 12$ is reached. The two phases that have formed are separated, and 20 ml of toluene are added to the aqueous bottom phase, stirring the mixture for 15 min. The phases are once more separated, and the aqueous phase is brought to pH 1 by addition of 33% HCl. The aqueous solution is then dripped on 300 ml of methanol. The solid that precipitates is filtered and washed with 50 ml of methanol.

To the filtered solid there are added 70 ml of deionized water, and the mixture is heated to 80° C. and kept under these conditions for 1 hour. Then the solution is cooled to room temperature. A white solid precipitates, which is filtered and washed with 20 ml of deionized water to obtain 4.2 g of the desired product, which is dried at 50° C. under vacuum for 6 hours. The weight of the dry product is 2.8 g.

EXAMPLE 3

Preparation of Risedronic Acid

The same procedure of preparation as the one described in Example 3 is followed, using 5.4 g of 2.-(3-pyridyl)-acetic acid instead of 2-(1-imidazyl)-acetic acid; 3.5 g of the desired product are obtained.

EXAMPLE 4

Preparation of Sodium Pamidronate

The same procedure of preparation as the one described in Example 1 is followed, using 86.4 g of β-aminopropionic acid instead of γ-aminobutyric acid; 81.5 g of the desired product are obtained.

The invention claimed is:

1. A process for preparing bisphosphonic acids and their salts of formula

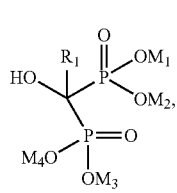

(1)

in which $R_1$ has the meanings indicated in the following Table 1:

| | |
|---|---|
| $R_1$ = CH3, | Etidronic acid |
| 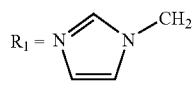 | Zoledronic acid |

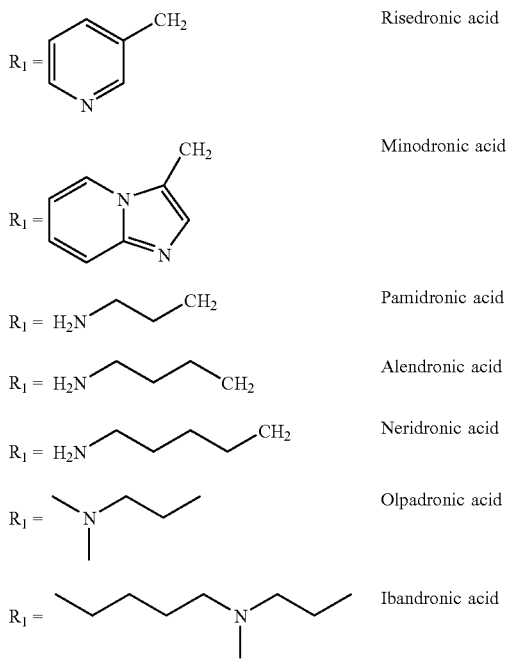

| | |
|---|---|
| Risedronic acid | |
| Minodronic acid | |
| Pamidronic acid | |
| Alendronic acid | |
| Neridronic acid | |
| Olpadronic acid | |
| Ibandronic acid | | and in which $M_1$, $M_2$, $M_3$, $M_4$ are selected from H, and a monovalent cation, comprising the reaction of acids of formula $R_1$-$CO_2H$, in which $R_1$ has the aforesaid meanings, with acids and phosphorus trichloride, wherein the reaction is conducted in ionic liquids as the reaction solvents, at a temperature of between 15° C. and 120° C. wherein said ionic liquids are selected from the group consisting of salts of ammonium, sulphonium or phosphonium having the following formulas

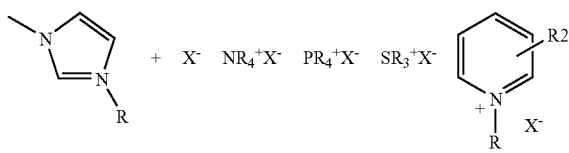

in which each R may be independently a linear or branched $C_1$—$C_{20}$ alkyl group, a cycloalkyl containing from 5 to 6 carbon atoms, alkylene aryl, or aryl; $R_2$ is H or a linear or branched $C_1$—$C_{18}$ alkyl group, $X^-$ is an anion selected the group consisting of halogenide, $BF_4^-$, $PF_6^-$, and $AlCl_4^-$.

2. The process according to claim 1, wherein the temperature at which the aforesaid ionic solvents are liquids is between 20° C. and 100° C.

3. The process according to claim 1, wherein $M_1$–$M_4$ are selected from the cations of an alkaline metal, H or the cations of aliphatic or cycloaliphatic amines.

4. The process according to claim 3, wherein $M_1$-$M_4$ are selected from H and/or sodium.

* * * * *